United States Patent [19]
Leuenberger

[11] Patent Number: 6,100,989
[45] Date of Patent: Aug. 8, 2000

[54] METHOD AND DEVICE FOR DETECTING DEFECTS IN TEXTILE WEBS

[75] Inventor: Rolf Leuenberger, Pfaffikon, Switzerland

[73] Assignee: Zellweger Luwa, Switzerland

[21] Appl. No.: 09/252,456

[22] Filed: Feb. 18, 1999

[51] Int. Cl.[7] .............................. G01N 21/84; H01L 27/00
[52] U.S. Cl. ........................ 356/430; 356/429; 250/208.1
[58] Field of Search ..................................... 256/429, 430, 256/431, 238.1; 250/208.1, 559.05, 227.3

[56] References Cited

U.S. PATENT DOCUMENTS 5,847,834 12/1998 Ho et al. ................................. 356/429
5,990,468 11/1999 Cornuejols ........................... 250/208.1

Primary Examiner—Frank G. Font
Assistant Examiner—Roy M. Punnoose
Attorney, Agent, or Firm—Burns, Doane, Swecker & Mathis, L.L.P.

[57] ABSTRACT

The invention relates to a method and a device for detecting defects in textile webs. In order to rapidly adapt devices of this type to widely varying textile webs and to be able to operate such devices simply, brightness values are determined from the web and are supplied directly to a filter constructed as a neural network. The output results of the neural network can be displayed as grayscale values to indicate detected defects.

12 Claims, 3 Drawing Sheets

METHOD AND DEVICE FOR DETECTING DEFECTS IN TEXTILE WEBS

This disclosure is based upon, and claims priority from, Swiss patent application No. 2029/96, filed Aug. 20, 1996, the contents of which are incorporated herein by reference.

This application claims priority under 35 U.S.C. §§119 and/or 365 to 2029/96 filed in Switzerland on Aug. 20, 1996; the entire content of which is hereby incorporated by reference.

FIELD OF THE INVENTION

The present invention relates to a method and a device for detecting defects in textile webs.

BACKGROUND OF THE INVENTION

Proposals for detecting defects in textile webs are described in the Textile Research Journal 63(4), pages 244–246 (1993) and 66(7), pages 474–482 (1996) under the titles: "Assessment of Set Marks by Means of Neural Nets" and "Automatic Inspection of Fabric Defects Using an Artificial Neural Network Technique". According to these publications, neural networks can be used for the detection of defects in textiles. In the disclosed methods particular input values are first determined for the network. Such input values include, for example, the distance between threads in the fabric at a given site or the mean value of this distance over the entire fabric, the standard deviation from values for the distance, the yarn mass and intensity values, which are derived from a fabric image subjected to Fourier transformation. These are all measurement values which must first be obtained from values derived from the fabric by way of more or less extensive calculations.

A disadvantage of methods of this type resides in the fact that they are not very flexible, so that the detection of defects in different fabrics requires calculations which need to be carried out in advance. Thus, it is not possible to derive or deduce input values from the web for a defect detection system which are adequate for all possible types of web texture. If an approximation of this method is nevertheless to be achieved, then a very large number of different measurement values must be determined, resulting in a correspondingly high calculation outlay. High speed and high cost computers are required to this end.

A method for detecting errors in lace is disclosed in Sanby et al, "The Automated Inspection of Lace Using Machine Vision," Mechatronics, Vol. 5, No. 2/03, Mar. 1, 1995. In this method, values for the intensity or brightness of scanning points of a picture of the original lace are compared to those of an error-free or reference picture. Values of the differences are calculated and fed to a threshold stage. Scanning points of the picture showing greatly differing values trigger an output signal. Such trigger signals are especially generated in the region of errors in the lace. Due to geometric distortion of the pictures, many apparent (but not real) errors will be detected or signaled. Therefore, a neural network is used for discriminating apparent errors from real errors. Scanning points belonging to a small area surrounding one trigger pixel are fed to the neural network, which acts as a classifier. The network is also fed with pixels and corresponding brightness values from the original picture and from the reference picture. From these three sets of pixels, the network determines if the trigger pixel is really indicating an error or not.

One drawback of this method resides in the fact that first a preliminary discrimination of errors in the lace is performed by comparing brightness values of pixels alone. Subsequently, the neural network confirms the preliminary discrimination. For that task, three sets of data must be fed to the network in order to obtain a definitive judgment. This method is not suited for inspecting textiles such as woven fabric or other types of cloth which do not show a periodically repeating structure in an image. Compared to lace, such textiles have textures wherein errors are only distinguished by modifications of the texture. Methods using differences in images do not give acceptable results. A subsequent classification in neural networks is not useful in this context.

The present invention attains the object of providing a method and a device which can be rapidly adapted to widely varying textile webs and is simple to operate.

This objective is attained by way of the skillful use of modern, cost-effective computers operating in parallel. The web is scanned in known manner, for example line-by-line, by a camera which supplies data to a memory. Values for the brightness or intensity of scanning points or partial areas of a web are stored in the memory. In this manner, the memory eventually contains an image of a section of the web. Values from connected areas are then retrieved in parallel from the memory and supplied in parallel to a neural network, which is trained to recognize defects. The neural network indicates whether there is a defect in the examined area. This result is read into a further memory, which stores this result, taking into account the position of the area on the web. As the examined areas gradually cover the entire width of the web and therefore also cover the web over a section of its longitudinal direction, conclusive data regarding defects in the examined section is eventually available.

In accordance with the invention, a neural network of a type that is known per se is used as a non-linear filter and operates directly with brightness values from a relatively large environment (e.g. 10×100 pixels) as input values for the neural network, without the need for additional measurement values. The environment is displaced pixel-by-pixel over the surface of the web, so that a filtering operation is carried out. At the output of the neural network a filtered image of the examined area is produced, in which the novel structure of the fabric is attenuated and errors are clearly identified. By means of a learning process, both the filter structure and the filter parameters are automatically determined and in this manner adapted to any type of textured and small-patterned surfaces. The learning process can be effected by the presentation of approximately 20 to 100 image patterns which contain defects, and the same number of image patterns containing no defects. By dividing the filter into two neural networks for input environments which are oriented in the warp or weft direction in the case of wovens, the distinction between warp and weft defects can be further supported.

The advantages attained by this invention can be seen in particular in that a device of this type can be constructed from cost-effective, simple computers which operate in parallel and are optimized for neural networks. As a result of the parallel processing of all input values, very high computing capacities (e.g. several Giga MAC (multiply accumulate calculations)) are attained, so that the result of the examination can also be continuously determined even at high product web velocities. Computers of this type can be extensively integrated in a single silicon chip and used in the form of add-on boards in personal computers. Examples of circuit boards of this type would be the PALM PC board made by the company Neuroptic Technologies, Inc and the CNAPS PC board made by the company Adaptive Solutions. In this manner, high inspection speeds of, for example, 120 m/min are possible.

The learning process can be effected very simply with the aid of a web section recognized as defect-free by the eye and defective sections of the web. In addition, the sensitivity of the defect detection can be increased by the particular form and orientation of the areas from which input values are derived. Using a simple learning process, a high degree of adaptability to differently textured webs is possible. No specially trained personnel are required for the simple operating procedure. The invention can be used for textured and patterned surfaces.

BRIEF DESCRIPTION OF THE DRAWINGS

The invention will be explained in further detail hereinafter by way of an example with reference to the attached drawings, in which.

DETAILED DESCRIPTION

Figure 1:
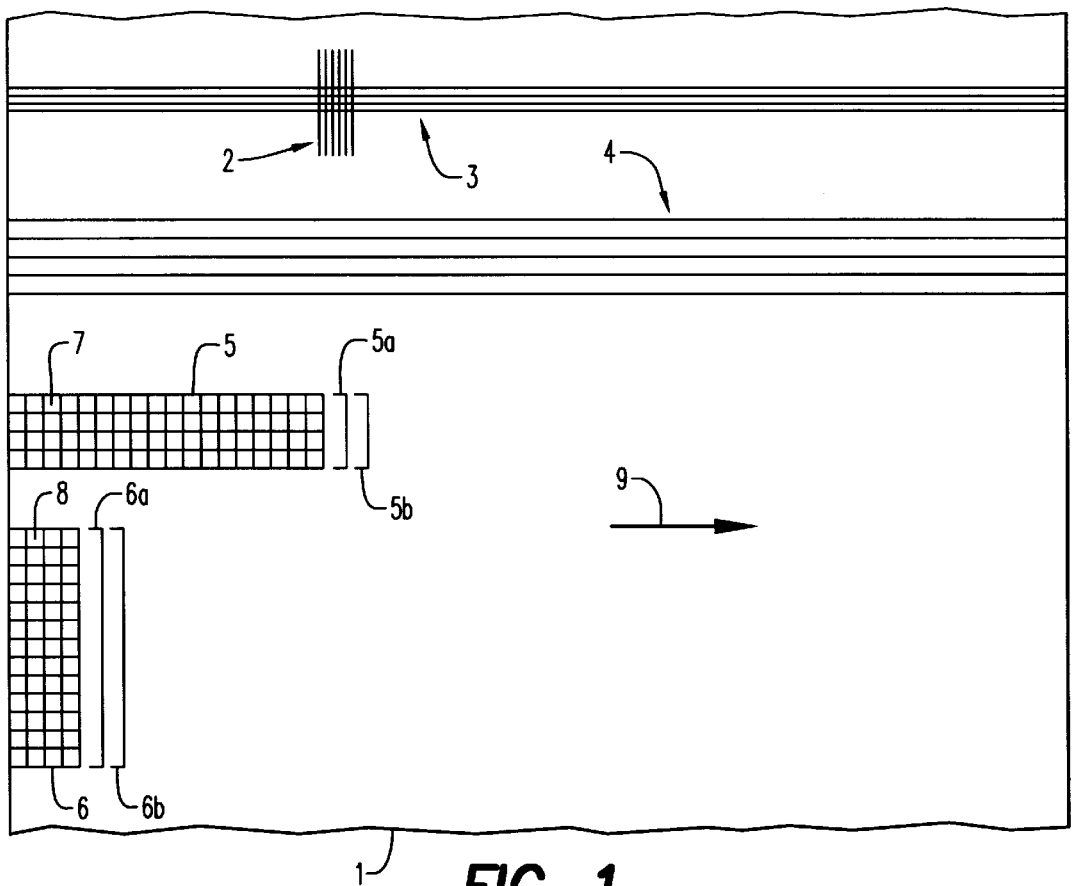
FIG. 1 shows part of a textile web on which different features are schematically indicated.

FIG. 1 shows part of a web 1, in this case a woven fabric, for example, which is formed of warp threads 2 and weft threads 3, of which only a few are illustrated. In addition, a plurality of lines 4 are shown, as can be covered for example by a line camera, which scans the web 1 in such a manner that the entire web is covered. Lines 4 of this type can also overlap so that no gaps are left between the lines. In addition, areas 5 and 6 can be seen, which are formed by 72 partial areas 7 and 56 partial areas 8, respectively. Areas 5, 6 of this type are only defined for a given period of time and are therefore defined for other periods of time in the same form and size, but in different positions. 5a, 5b and 6a, 6b indicate such further areas in other positions, with a plurality of areas 5, 5a, 5b and 6, 6a, 6b being defined for successive overlapping intervals. These areas preferably extend with time in the direction of an arrow 9 over the width of the web 1 in such a manner that successive areas 5, 5a, 5b and 6, 6a, 6b are offset relative to one another by one partial area 7, 8.

Figure 2:
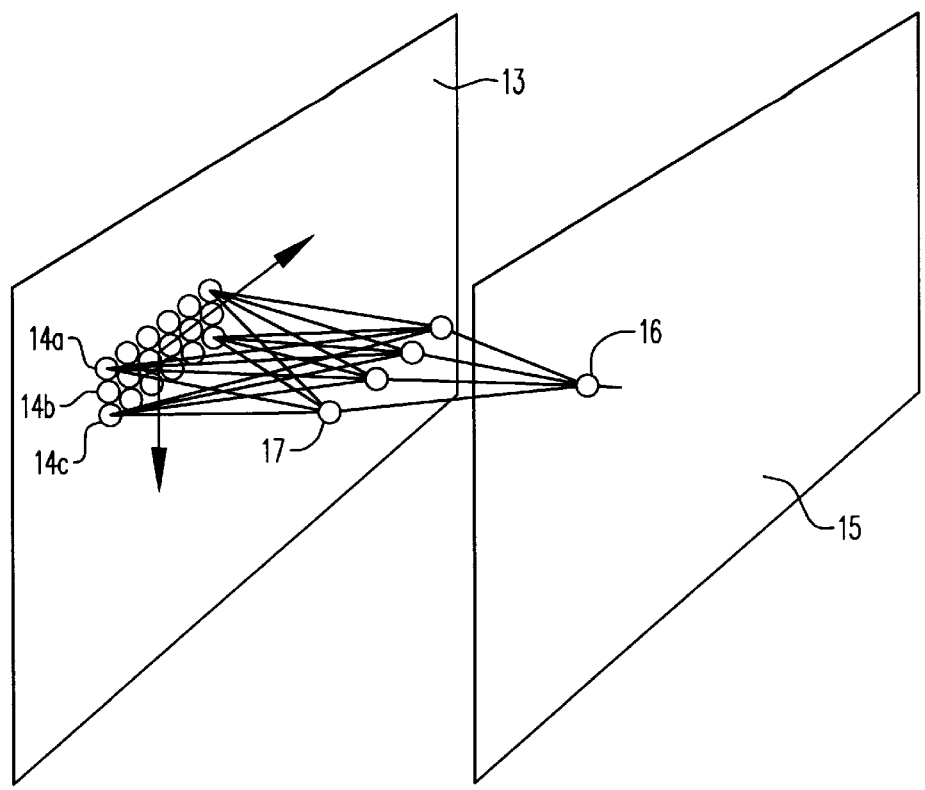
FIG. 2 is a schematic illustration of a non-linear filter operation.

FIG. 2 figuratively illustrates the contents of a memory in a plane 13, with input values 14a, 14b, 14c, etc., which represent the brightness or a grayscale value of the web as detected by a sensor or a camera. In a plane 15, signals are illustrated as output values or results, only one signal 16 being visible in this case, which indicates the probability that a defect is present in a corresponding area of the web. Arranged between the planes 13 and 15 is a non-linear filter operation, when this drawing is viewed in terms of function. However, the drawing can also be viewed as showing the structure of a device. In this case, 17 designates an intermediate computer and 16 an output computer. The input values 14 can also be seen as input neurons, the intermediate computers 17 as hidden neurons and the output computers 16 as output neurons of a neural network.

Figure 3:
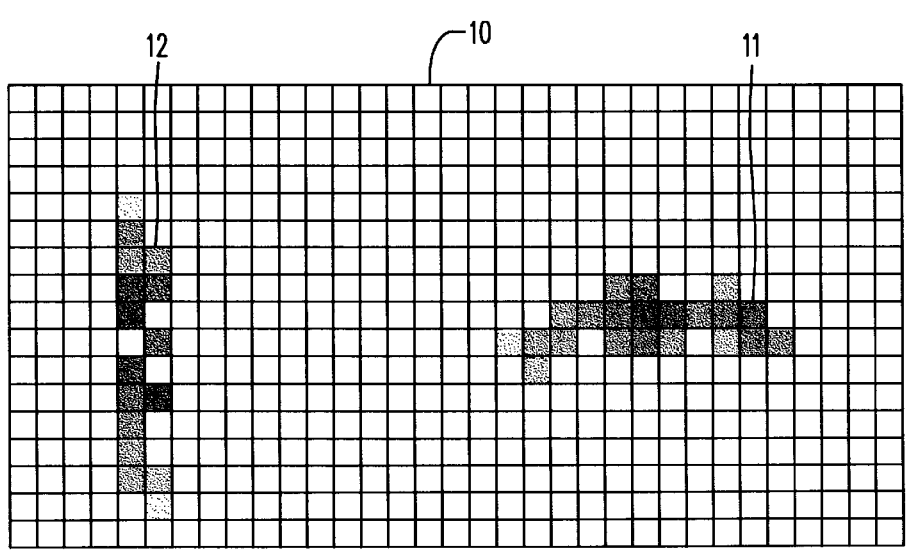
FIG. 3 is an image of portions of a web with defect markings.

FIG. 3 is an enlarged view of an output image 10 of a section of the web 1. Two regions 11 and 12 containing defects are marked on the image 10 by means of darker grayscale values. These regions 11, 12 are composed of partial areas according to FIG. 1, so that, as shown in the drawing, a plurality of partial areas are occupied by a defect signal and together produce the regions 11 and 12.

Figure 4:
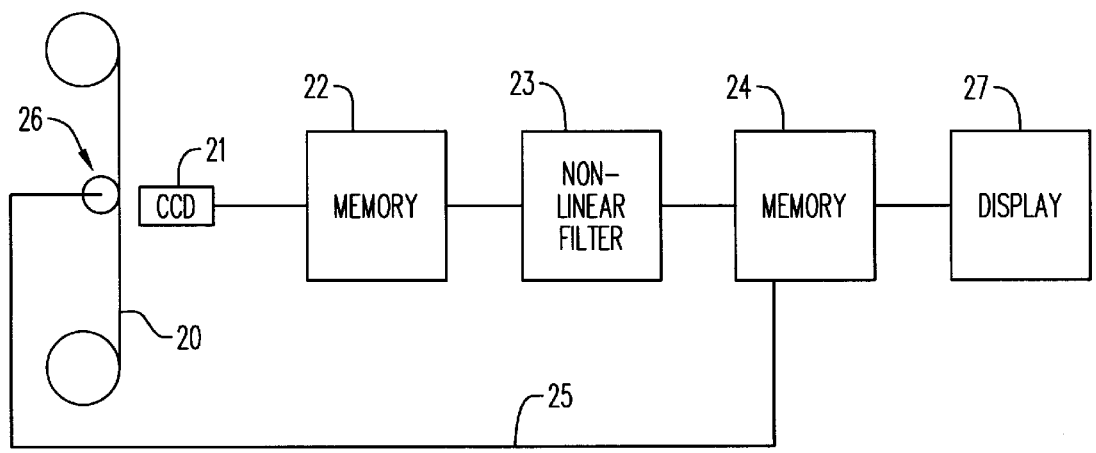
FIG. 4 is a schematic illustration of a device according to the invention.

FIG. 4 is a schematic illustration of the configuration of a device according to the invention. The latter comprises a camera 21 arranged directly adjacent the web 20, e.g. a CCD camera or more generally a photoelectric converter, which is connected to a memory 22. Signals from a plurality of adjacent lines 4 are stored in the memory 22 for a given period of time. These signals and lines are stored in the memory 22 according to the FIFO principle. The memory 22 is connected to a non-linear filter 23, which can be constructed for example as a computer, in which a corresponding filter program is loaded. The filter program is designed according to the principles of a neural network. The latter is connected to a memory 24, in which defect signals (or no-defect signals) are stored with their allocation to areas on the web. Also in this case, the defect signals remain stored in the memory 24 for a given period of time and the defect signals are also processed according to the FIFO principle. The memory 24 is connected via a connection 25 to a distance recorder or length encoder 26, so that data relating to the instantaneous position of the camera 21 along the web 20 can be fed into the memory 24. In order to display the results of the examinations of the textile web 20, a display unit 27 is connected to the memory 24, which can be constructed for example as a printer or monitor. However, a processing unit, e.g. a computer, can also be provided in place of the display unit 27, which processing unit subjects the content of the memory 24 to a further classification, namely so that defect regions such as the regions 11 and 12 from FIG. 3 can be compared with given criteria, so that they can be associated with different types of defects. For example, in the case of wovens, the defects can be classified into weft and warp defects. The region 11 in FIG. 3 would therefore indicate a weft defect and the region 12 a warp defect.

Figure 5:
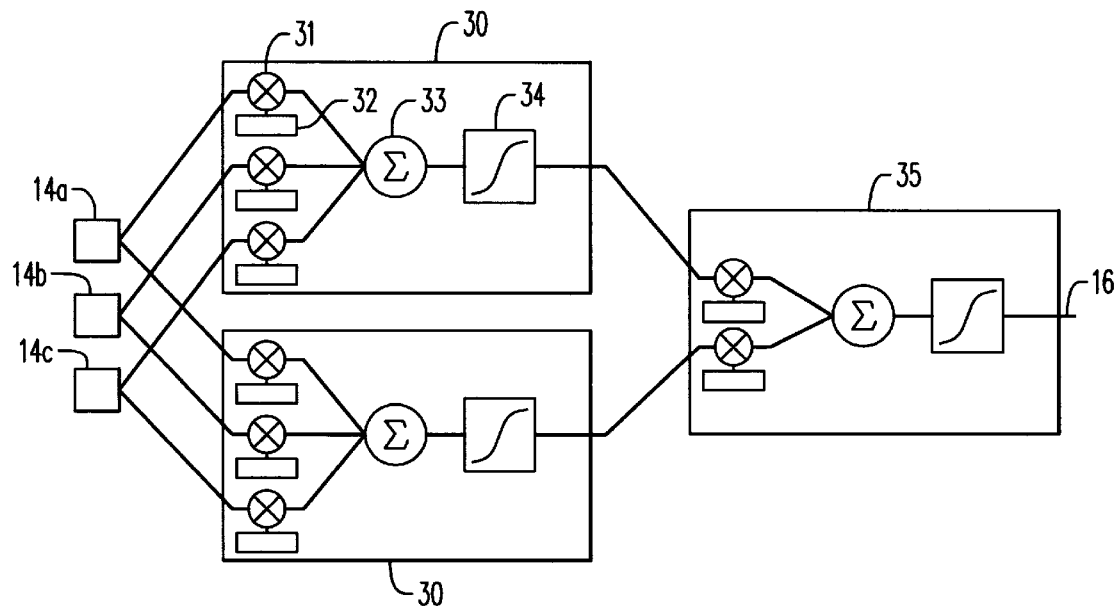
FIG. 5 is a schematic illustration of part of the device.

FIG. 5 shows a section of a non-linear filter 23 (FIG. 4), the filter being constructed in this case as a neural network. It comprises processors 30 arranged in a first layer and processors 35 arranged in a second layer. In relation to FIG. 2, the processors 30 can be regarded as exemplary embodiments for the intermediate computers 17 and the processors 35 for the output computers or output neurons 16. The processors 30 are constructed from a plurality of multipliers 31 with associated memories 32, which are all connected to an adder 33. This is in turn connected at its output to a processing stage 34, which has a nonlinear characteristic curve. The multipliers 31 are connected to the memory 22 for receiving input values 14a, 14b, 14c, etc. The processors 35 are constructed in like manner, although the processing stages 34 of the processors 30 are connected to the multipliers 31 of the processors 35. The latter comprise an output 16 for output values. The illustrated arrangement, in which the processors 30 of the first layer are acted upon by all input values of an area, is realized in this case as a parallel computer, which comprises a number of the same types of processors 30, 35.

The method of operation of the method and device according to the invention is as follows: In relation to the web 1, areas 5, 6 are first defined in the memory 22 by means of instructions that are preset in the memory or in the filter 23 connected thereto, which determine from which memory locations in the memory 22 values are taken and supplied as input values for the filter 23. On the one hand, such areas 5, 6 should have sides lying parallel to the lines 4 recorded by the camera 21 from the web 1. On the other hand, the areas should preferably also have a main direction which lies parallel to the texture features of the web 1. In this case, the area 5 lies with its main direction parallel to the weft threads 3 and the area 6 parallel to the warp threads 2.

A learning phase then follows in order to adjust the filter coefficients or filter parameters, in a known manner associated with neural networks. In this phase, the camera 21 is aimed alternately at areas containing no defects and areas containing a defect. The result which should be displayed by the filter 23 is predetermined in each case. For instance, if no defects are present, the output nodes 16 of the filter could all produce a binary zero value, whereas if a defect is present the nodes which correspond to that area of the web could generate a binary one value. In the learning phase, the computer, which acts as the filter, is operated in a mode in which it does not transmit results but adapts its coefficients and parameters from the desired results and the input values. The coefficients and parameters are first predetermined as output values, for example as values in the memories 32 or as parameters of the non-linear characteristic curve of the processing stage 34, and are adapted by the learning process according to given techniques for training a neural network, so that the filter receives a specific transmission function. For instance, the training of the neural network can be carried out using the known techniques of error back propagation and simulated annealing. A description of these techniques can be found in Hertz et al, "Introduction to the Theory of Neural Computation", Santa Fe Institute Studies in the Sciences of Complexity, Lecture Notes, vol. 1, Addison-Wesley, 1991. This training process is preferably repeated each time a new web 1, 20 is presented.

Once the learning phase is complete, the mode in the computer is changed and the detection of the defects can be carried out on a web 1 which is moved in a direction perpendicular to the arrow 9. This means that the camera now passes over the web 1 in a manner known per se, and therefore not illustrated in further detail, in the direction of the arrow 9, and thereby optically scans lines 4. The recorded values for the brightness or color intensity are supplied to the memory 22, which also stores these values in lines, for example. The values for all partial areas 7, 8 from areas 5, 5a, 5b, 6, 6a, 6b etc. are supplied in parallel from the memory 22 to the filter 23, which for each area 5, 5a, 5b, 6, 6a, 6b transmits an output value, result or signal 16. This signal indicates the probability that a defect is present in the corresponding area of the web. For instance, the probabilities might be expressed as a decimal value in the range 0.0–1.0. Referring to FIG. 3, the probabilities are shown as multi-level grayscale values, where a low probability corresponds to a lighter area and a high probability is shown as a dark area. Intermediate probabilities have corresponding grayscale values. This signal is read into the memory 24 together with data relating to the position of the area from which the signal is derived, and is stored for a period of time required by the camera 21 in order to cover a plurality of lines 4. Thus, the signals are stored in the memory 24 in storage locations associated with relative positions on the web, so as to correspond to an image 10 as shown in FIG. 3. Within this image 10 signals 16 are recognizable, which, since they are usually not isolated but occur in groups, are combined to form regions 11, 12 indicating a defect in the web 1. This image 10 can also be made visible on a display unit 27.

Figure 6A:
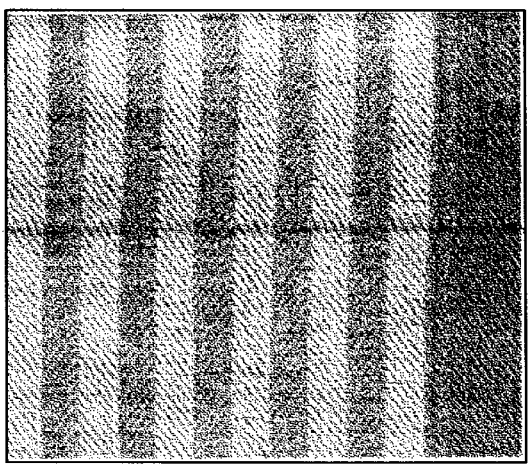
FIGS. 6a and 6b are input and output images, respectively, pertaining to a web having a defect.
Figure 6B:
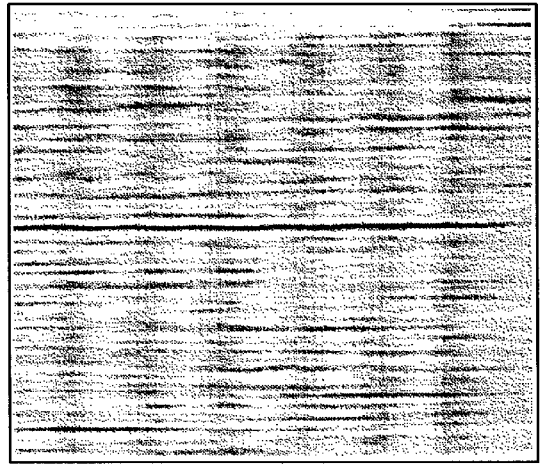

FIGS. 6a and 6b illustrate, respectively, an input image of a larger portion of a web having a horizontal stripe defect and the corresponding grayscale output image which is produced. As can be seen, the defect is readily identifiable from a simple comparison of brightness values in the output image.

If a processing unit is provided instead of the display unit 27, the processing unit is constructed as a computer which can carry out an image segmentation in order to combine individual pixels to form regions according to a suitable method, as described for example in "Rafael C. Gonzalez and Paul Wintz: Digital Image Processing, Addison-Wesley Publishing Company, Reading Mass. 1987".

If the non-linear filter 23 has a construction according to FIG. 5, then input values 14a, 14b, 14c, etc., selected according to the areas 5, 6 are all supplied to each of the processors 30 of the first layer. Each processor 30 therefore comprises the same number of multipliers as the number of partial areas in the sensed area. In the multipliers, the input values 14 are multiplied by factors which are stored in the memories 32 and then added in the adder, so that a mixed value is produced, which is composed of all input values of an area. This mixed value is further changed by the non-linear characteristic curve of the processing stage 34. The adapted mixed values are in turn supplied to the processors 35 of the second layer, where they are processed in the same manner as in the processors 30. An output value for each area is produced at the output 16. These output values are supplied to the memory 24 where they are distributed as illustrated in FIG. 3.

Although the invention is explained herein by way of example of a woven fabric, it is equally possible to use the invention with knitted or similarly textured webs. In that case, particular attention should be paid to ensure that the areas 5 and 6 are aligned so that their main axes lie parallel to prominent lines in the pattern or knitting. In this respect, it is also possible to arrange the main axes of the areas 5, 6 in any manner (not at right angles) and to select a direction for the progression or displacement of the areas other than that according to the arrow 9.

What is claimed is:

1. A method for detecting defects in textile webs comprising the steps of:

sensing brightness values for a plurality of partial areas within an area of a textile web;

processing said brightness values in parallel as input values in a non-linear filter operation; and generating a signal as the result of the filter operation which indicates the probability of a defect in the area.

2. A method according to claim 1, characterized in that all partial areas of an area form input values and further areas, which overlap with previously formed areas, are formed at intervals.

3. A method according to claim 1, characterized in that the filter operation is carried out in a neural network capable of learning.

4. A method according to claim 1, characterized in that the areas comprise a main direction lying parallel to texture features of the web.

5. A method according to claim 1, characterized in that input values are determined from a plurality of differently oriented areas.

6. A method according to claim 1, characterized in that filter coefficients for the filter operation are initially predetermined at random and are then modified in a learning process.

7. The method of claim 1 further including the step of producing a display of grayscale values corresponding to the probability signals of respective areas of the web.

8. A device for detecting defects in textile webs, comprising a series connection of an image recording device, a first memory for brightness values of a plurality of partial areas of a textile web, a non-linear filter which receives the brightness values stored in said first memory as input values and generates signals to indicate the probability that a defect is present in the textile web, and a second memory storing values associated with defects.

9. A device according to claim 8, characterized in that said non-linear filter is a neural network.

10. A device according to claim 9, characterized in that the neural network is constructed as a parallel computer.

11. A device according to claim 10, characterized in that the parallel computer is formed by a plurality of like processors.

12. A device according to claim 8, further including a display device which generates a display of plural grayscale values corresponding to the probabilities of defects in respective areas of the web.

* * * * *